United States Patent [19]

Wardlaw

[11] 4,188,950
[45] Feb. 19, 1980

[54] DISPOSABLE SYRINGE

[76] Inventor: Stephen C. Wardlaw, 128 Sunset Hill Dr., Branford, Conn. 06405

[21] Appl. No.: 955,774

[22] Filed: Oct. 30, 1978

[51] Int. Cl.² ............................................. A61M 5/00
[52] U.S. Cl. ................................................ 128/218 F
[58] Field of Search ........... 128/218 R, 218 F, 218 C, 128/218 D, 218 DA, 215, 216, 213, 220, 221

[56] References Cited

U.S. PATENT DOCUMENTS

| | | | |
|---|---|---|---|
| 3,605,744 | 9/1971 | Dwyer | 128/218 F |
| 3,890,971 | 6/1975 | Leeson et al. | 128/218 R |
| 3,893,608 | 7/1975 | Koenig | 128/218 R |

*Primary Examiner*—John D. Yasko
*Attorney, Agent, or Firm*—William W. Jones

[57] ABSTRACT

An improved disposable syringe having provisions for rendering the needle incapable of harming one when the unit is discarded. The syringe operates with a retracted needle which is driven to a protruding position when the device is used. After use the needle is retracted from the protruding position and bent so as to prevent the needle from harming anyone after the unit is discarded, and to prevent reuse of the needle.

11 Claims, 5 Drawing Figures

DISPOSABLE SYRINGE

This invention relates to an improved disposable hypodermic syringe which is non-reusable and which has a safety feature preventing the needle from harming anyone once the device is thrown away after use. In its preferred form, this invention relates to an improved syringe of the type disclosed in copending application Ser. No. 955,773, filed Oct. 30, 1978.

There is a distinct need in the medical field for a disposable hypodermic syringe which can be factory pre-loaded with an accurately measured amount of a medicament and then safely store the medicament for an extended period of time, on the order of one year or more. This type of syringe could be used by both trained and untrained persons, and if made to operate automatically, could be used by laymen to self administer injections, or to administer injections to others. Such a hypodermic syringe is described in co-pending application Ser. No. 955,773, referred to above.

One problem to be solved with such syringes relates to the needle which is left projecting from the syringe after the latter is used. This presents a potential problem of possible injury being inflicted upon someone after the syringe is discarded. One solution to the projecting needle problem which has been offered by the prior art involves the use of a return spring which automatically retracts the needle after the main spring has driven the needle out of the syringe housing. This solution; however, requires a delicate balancing of spring forces so as to insure that the injection is administered at the proper time and in a proper sequence. This balancing is not readily achieved in a mass produced, disposable item designed for but a single use. For this reason, the spring return concept has been featured in automatic syringe devices which are designed for repeated usage and which, therefore can be made at the higher cost needed to provide the necessary accurate spring forces.

Furthermore, a solution to the protruding needle problem which involves a retracting of the needle which at least partially resets, or recocks the device is not desirable with a disposable unit because such enables the device to be reused for possibly illicit purposes.

My solution for this problem is to provide means on the syringe which, upon actuation, retracts the needle from its protruding position while also deforming the needle by bending it so that the needle cannot be reused or even separated from the syringe easily. Thus, the needle presents no possible injury problem, nor can it be any way used for possibly illicit purposes after the device has been used for its intended purpose.

A movable member is connected to the base of the syringe. The member permits the needle to move from its retracted position to its fully extended position to administer the injection, and is then manipulated to bend the needle in a direction lateral to its axis and, at the same time, pull it back from its extended position to a safe position wherein it is covered completely by the member, whereby it cannot harm anyone, and it cannot be reused, or even readily removed from the syringe. The member, which can be termed a retracting member, or a retracting-deforming member, is inexpensively made, and does not appreciably increase the size or weight of the syringe.

It is therefore, an object of this invention to provide an improved disposable syringe wherein the needle is rendered incapable of causing injury after the device is used so that the device may be safely discarded.

It is a further object of this invention to provide an improved syringe of the character described wherein the extended needle is retracted and bent so as to be rendered unusable.

It is yet another object of this invention to provide an improved syringe of the character described wherein the needle retracting-bending means is formed as an assembled part of the syringe which may be easily actuated after the device is used.

These and other objects and advantages of this invention will become more readily apparent from the following detailed description of a preferred embodiment of a device formed in accordance with the invention, taken in conjunction with the accompanying drawings, in which.

Figure 1:
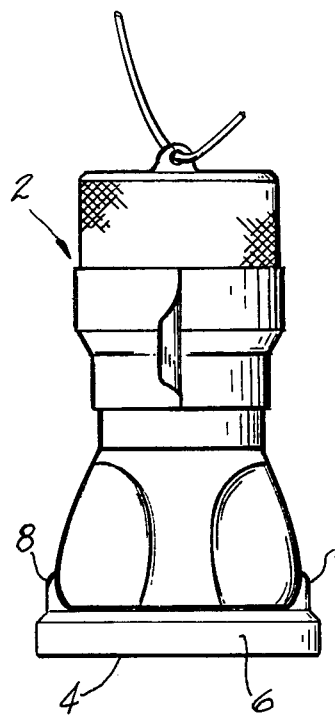
FIG. 1 is a side elevational view of a preferred embodiment of an automatic disposable syringe having a needle retracting member formed as a part thereof.

Referring now to FIG. 1, there is shown a preferred embodiment of an automatic, disposable hypodermic syringe having a needle retracting feature formed in accordance with this invention. The syringe 2 has a construction which is set forth in detail in co-pending application Attorney's Docket No. H-1018; therefore, said construction, will not be repeated in detail herein except for certain features thereof which are useful for explaining the operation of the needle retractor. The end surface 4 of the syringe 2 can be termed the bottom surface, i.e., the surface which is pressed against the skin of the user, when administering the injection. The bottom surface 4 of the syringe 2 is formed by a disk 6 which is movably mounted on the remainder of the syringe 2. A pair of tabs 8 engage recesses 10 (see FIG. 2) in the syringe 2 to properly help index and retain the disk 6 properly oriented with respect to the remainder of the syringe 2.

Figure 2:
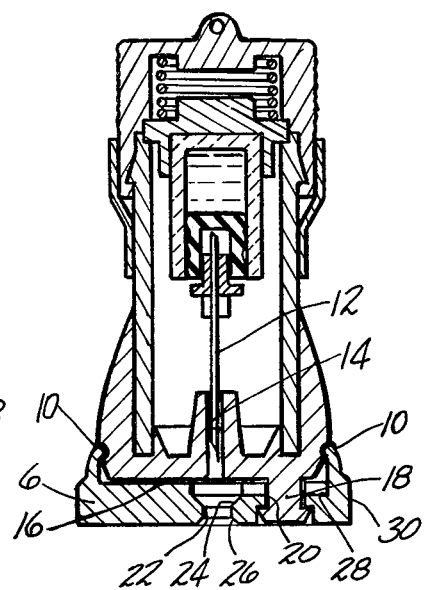
FIG. 2 is an axial sectional view of the syringe of FIG. 1 showing details of the needle retracting portion thereof, the device being shown in a cocked, ready-to-use condition.

As shown in FIG. 2, the syringe 2 has a retracted needle 12 aligned with a bore 14 through which the needle 12 is driven to administer the injection. A tape strip 16 closes the bore 14 to preserve the sterility of the interior parts of the syringe, the tape 16 being pierced when the needle 12 is driven to its protruding position to administer the injection. The lower portion of the syringe 2 is formed with a projecting post 18 which extends through a hole 20 in the disk 6. Thus the disk 6 is able to pivot about the post 18 with respect to the remainder of the syringe 2; however, the disk 6 is indexed and held in the position shown in FIGS. 1 and 2 by the tabs 10. The disk 6 also includes a through passage 22 which is coaxial with the needle 12 and bore 14 when the disk 6 is indexed to the position shown in FIG. 2. The passage 22 is provided with chamfered ends at 24 and 26 to help prevent snagging of the needle 12 when the latter is retracted after use. The upper surface of the disk 6 is formed with a closed circular slot 28 which extends radially from the passage 22, stopping short of the side wall 30 of the disk 6. It will be noted that the post 18 extends through the slot 28, the slot 28 being wider than the post 18 so as not to inhibit rotation of the disk 6 with respect to the remainder of the syringe 2.

Figure 3:
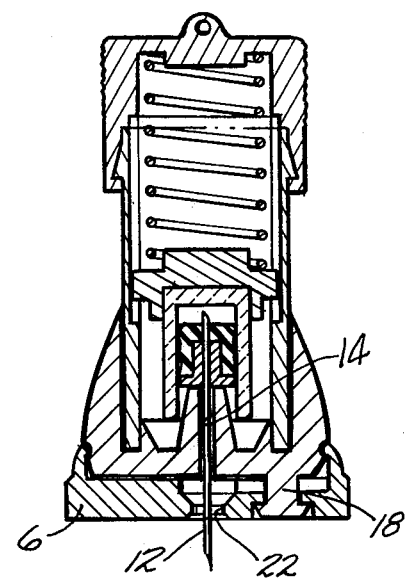
FIG. 3 is an axial sectional view similar to FIG. 2, but showing the device in a "fired" condition as it appears after an injection has been administered, and the needle has been driven to a position wherein it protrudes from the syringe housing.
Figure 4:
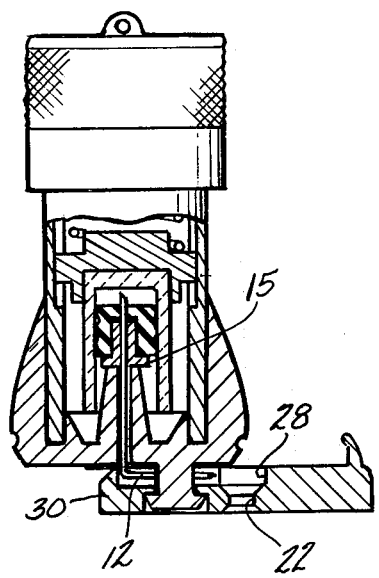
FIG. 4 is an axial sectional view similar to FIG. 3, but showing the initial phase of actuation of the needle retracting portion of the device.
Figure 5:
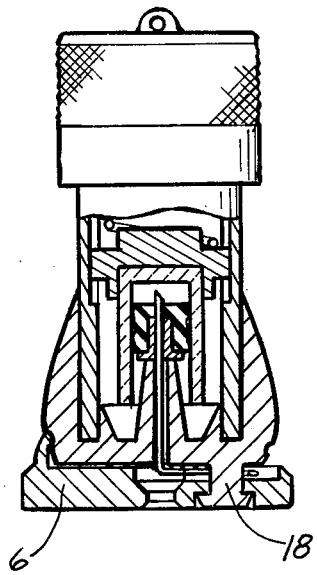
FIG. 5 is an axial sectional view similar to FIG. 4 showing the final stage of operation of the needle retracting portion of the device, wherein the device is ready to discard.

It will be appreciated that, with the parts in their respective positions shown in FIG. 2, the device is in a cocked and ready-to-use condition. Upon the administering of an injection, the parts of the syringe 2 move to the respective positions shown in FIG. 3, wherein the needle 12 protrudes from the syringe 2 a predetermined distance through the bore 14 and the disk passage 22. After the injection has been administered, the needle 12 is retracted by turning the disk 6 through a 360° revolution about the post 18, from the position shown in FIG. 3 to the position shown in FIG. 4, and on to the position shown in FIG. 5. It will, of course, be noted that the axis of rotation, e.g., the axis of the post 18 and hole 20, of the disk is radially offset from the axis of the needle 12 and disk passage 22. Thus when the disk 6 is rotated about the post 18, the passage 22 is swept along an arcuate path and the wall of the passage 22 bears against the protruding needle 12 and bends the latter. Since the needle 12 cannot be pulled through the bore 14 due to an enlarged ferrule 15 secured to the needle, movement of the passage 22 through its arcuate path will cause the needle 12 to be drawn back through the passage 22 and preferably into the slot 28, as shown in FIG. 4. It will be noted that the substantially circular shape of the slot 28 ensures that, during rotation of the disk 6, the outer edge of the slot 28 will remain below the bore 14 so that the needle 12 can be smoothly fed into the slot 28 through the passage 22. Engagement of the needle 12 by the passage 22 and the side wall of the slot 28 will bend the needle 12 and render it un-reusable. If the needle 12 is long enough, rotation of the disk 6 back to the position shown in FIG. 5 will preferably wrap the needle 12 to some extent around the post 18. It will be noted that only a single tab 10 could be used, or the tabs 10, if two are used, can be break-away tabs so as not to interfere with rotation of the disk 6.

It will be readily appreciated that the bent, retracted needle is completely covered by the remainder of the device so that it cannot cause harm to anyone. The retractor is a part of the syringe, so that it cannot be left behind when the syringe is carried about prior to use. The syringe housing part, which includes the post 18 is preferably made of injection molded plastic, as is the disk 6. The disk 6 can simply be pressfitted onto the post 18 and the tabs 8 properly aligned when the device is assembled. It will further be appeciated that the improved syringe of this invention includes an inexpensive, dependable needle retractor feature which renders the syringe harmlessly disposable.

Since many changes and variations of the disclosed embodiment of the invention may be made without departing from the inventive concept, it is not intended to limit the invention otherwise than as required by the appended claims.

What is claimed is:

1. An improved automatic disposable syringe adapted to be used but once, said syringe comprising:
   (a) a housing containing an ampoule and hypodermic needle, said needle being disposed in a retracted position completely within the confines of said housing;
   (b) means in said housing for driving said needle to an injecting position wherein said needle protrudes from said housing; and
   (c) retracting means movably mounted on said housing, said retracting means being operable to engage said needle and bend the latter to pull said needle from its protruding position to a safe position wherein said needle is covered over by a portion of said syringe.

2. An improved automatic disposable syringe adapted to be used but once, said syringe comprising:
   (a) a housing containing an ampoule and hypodermic needle, said needle being disposed in a retracted position completely within the confines of said housing;
   (b) means in said housing for driving said needle through a needle port, in said housing to an injecting position wherein said needle protrudes from said housing; and
   (c) a retracting member movably mounted on said housing, said retracting member being disposed on said housing in a position wherein said needle port is unblocked for passage therethrough of said needle and said retracting member being movable laterally across said needle port to engage said needle as it protrudes through said needle port and bend said needle and pull the latter to a safe position wherein said needle is covered by a portion of said syringe.

3. An improved automatic disposable syringe adapted to be used but once, said syringe comprising:
   (a) a housing containing an ampoule and hypodermic needle, said needle being disposed in a retracted position completely within the confines of said housing, one end of said housing being formed with a needle port;
   (b) means in said housing for driving said needle to an injecting position wherein said needle protrudes from said housing through said needle port; and
   (c) a disk mounted adjacent to said one end of said housing, said disk being movable across said one end of said housing but being secured to said housing so as not to be readily detachable therefrom, said disk being movable from a first position wherein said needle port is unblocked for passage of said needle therethrough to a second position wherein said disk moves laterally across said needle port to engage the protruding needle and bend the latter thereby retracting the needle out of its protruding position to a safe position wherein said needle is completely covered by a portion of the syringe.

4. An improved automatic disposable syringe adapted to be used but once, said syringe comprising:
   (a) a housing containing an ampoule and hypodermic needle, said needle being disposed in a retracted position completely within the confines of said housing, one end of said housing being formed with a needle port;
   (b) means in said housing for driving said needle to an injecting position wherein said needle protrudes from said housing through said needle port; and
   (c) a retractor member movably mounted on an external surface of said one end of said housing, said retractor member being secured to said one end of said housing so as not to be readily removable therefrom, said retractor member being movable from a first position wherein said needle port is unblocked to allow passage of said needle therethrough to a second position wherein said retractor member moves laterally across said needle port to engage and bend the needle protruding therethrough until said needle is bent to a safe position wherein said needle is covered by said retractor member.

5. The syringe of claim 4, wherein said retractor member is provided with a through passage which is co-axial with said needle port when said retractor member is in said first position, the edge of said passage engaging said protruding needle when said retractor member is moved toward said second position.

6. The syringe of claim 5, wherein said retractor member is a disk mounted on said one end of said housing for rotation about an axis which is radially offset from the axis of said needle port.

7. The syringe of claim 6, wherein said disk is provided with an internal slot into which said through passage opens, said slot providing means for containing the bent needle.

8. The syringe of claim 6 further comprising detent means for releasably retaining said disk in its first position.

9. An improved automatic disposable syringe adapted to be used but once, said syringe comprising:
(a) a housing containing an ampoule and hypodermic needle, said needle being disposed in a retracted position completely within the confines of said housing, one end of said housing being formed with a needle port, a post formed on said one end of said housing, said post being radially offset from said needle port;
(b) means in said housing for driving said needle to an injecting position wherein said needle protrudes from said housing through said needle port;
(c) a tape secured to said one end of said housing overlying said needle port to maintain sterility in the interior of said housing;
(d) a needle retractor disk mounted on said post, said retractor disk overlying the majority of said one end of said housing and having a through passage which is coaxial with said needle port, said retractor disk providing an end surface of the syringe which is placed against the user's flesh when an injection is administered, and said retractor disk being rotatable about said post whereby said through passage is moved out of alignment with said needle port to move said retractor disk against the protruding needle to bend the latter and draw the needle back through said retractor disk through passage to a safe position wherein the bent needle underlies said retractor disk.

10. The syringe of claim 9, further comprising detent means for releasably holding said retractor disk in the position wherein said through passage and needle port are coaxial.

11. The syringe of claim 9, wherein said retractor disk is provided with a slot facing said one end of said housing and into which said through passage opens, said slot providing means for receiving the bent needle.

* * * * *